(12) United States Patent
Cabot

(10) Patent No.: US 10,349,956 B2
(45) Date of Patent: Jul. 16, 2019

(54) ARRANGEMENT AND METHOD USED IN THE PREPARATION OF THE PROXIMAL SURFACE OF THE TIBIA FOR THE TIBIAL COMPONENT OF A PROSTHETIC KNEE JOINT

(71) Applicant: Jonathan Peter Cabot, North Adelaide (AU)

(72) Inventor: Jonathan Peter Cabot, North Adelaide (AU)

(*) Notice: Subject to any disclaimer, the term of this patent is extended or adjusted under 35 U.S.C. 154(b) by 219 days.

(21) Appl. No.: 15/522,454

(22) PCT Filed: Oct. 28, 2015

(86) PCT No.: PCT/AU2015/000643
§ 371 (c)(1),
(2) Date: Apr. 27, 2017

(87) PCT Pub. No.: WO2016/065396
PCT Pub. Date: May 6, 2016

(65) Prior Publication Data
US 2017/0333058 A1 Nov. 23, 2017

(30) Foreign Application Priority Data
Oct. 29, 2014 (AU) .................................. 2014904324

(51) Int. Cl.
*A61B 17/17* (2006.01)
*A61F 2/38* (2006.01)
(Continued)

(52) U.S. Cl.
CPC ........ *A61B 17/1764* (2013.01); *A61B 17/025* (2013.01); *A61F 2/389* (2013.01);
(Continued)

(58) Field of Classification Search
CPC .... A61B 17/1764; A61B 17/025; A61F 2/389
See application file for complete search history.

(56) References Cited

U.S. PATENT DOCUMENTS

| 2003/0069591 A1* | 4/2003 | Carson ................. A61B 17/154 606/130 |
| 2003/0167090 A1* | 9/2003 | Chervitz ............... A61F 2/0805 623/13.14 |

(Continued)

FOREIGN PATENT DOCUMENTS

| EP | 1348382 B1 | 9/2005 |
| WO | 2011128657 A1 | 10/2011 |

*Primary Examiner* — Christian A Sevilla
(74) *Attorney, Agent, or Firm* — Renner Kenner Greive Bobak Taylor & Weber

(57) ABSTRACT

An arrangement for the preparation of the proximal surface of the tibia for a tibial component of a prosthetic knee joint including a tibial and femoral stability gap preparation plate having a plurality of user operable height adjustable extension tabs that define a stability gap. A stability gap guide drill plate adapted to act as a guide for a drill bit to drill a series of bore holes into the proximal surface of the tibia to a depth commensurate with the height adjustment of the user operable height adjustable extension tabs and a stability gap router plate adapted to allow a router to complete a final bone resection on the surface of the tibia to rout or cut away bone about each of the series of bore holes so as to provide a stable balanced complete angular movement between a tibial component and a femoral component of the prosthetic knee joint throughout an arc of motion from extension, mid-flexion and flexion.

17 Claims, 12 Drawing Sheets

(51) Int. Cl.
 *A61F 2/46* (2006.01)
 *A61F 2/30* (2006.01)
 *A61B 17/02* (2006.01)

(52) U.S. Cl.
 CPC ............ *A61F 2/461* (2013.01); *A61F 2/4684* (2013.01); *A61B 2017/0268* (2013.01); *A61F 2002/3055* (2013.01); *A61F 2002/30556* (2013.01); *A61F 2002/30601* (2013.01); *A61F 2002/4658* (2013.01); *A61F 2002/4661* (2013.01)

(56) References Cited

U.S. PATENT DOCUMENTS

| | | | |
|---|---|---|---|
| 2004/0122441 A1 | 6/2004 | Muratsu | |
| 2005/0020941 A1 | 1/2005 | Tarabichi | |
| 2006/0149277 A1 | 7/2006 | Cinquin et al. | |
| 2007/0219564 A1 | 9/2007 | Lavallee et al. | |
| 2008/0195110 A1* | 8/2008 | Plassy | A61B 17/154 606/88 |
| 2008/0275451 A1* | 11/2008 | McAllister | A61B 17/155 606/87 |

\* cited by examiner

ARRANGEMENT AND METHOD USED IN THE PREPARATION OF THE PROXIMAL SURFACE OF THE TIBIA FOR THE TIBIAL COMPONENT OF A PROSTHETIC KNEE JOINT

TECHNOLOGICAL FIELD

This invention relates to an improved arrangement and method in the preparation of the proximal surface of the tibia for the tibial component of a prosthetic knee joint.

More particularly this invention relates to the preparation of the proximal surface of the tibia such that the level and/or profiling of the final bone resection on the proximal surface of the tibia is such so as to provide balanced stability between the tibial component and the femoral component of the prosthetic knee joint to permit stable and balanced movement of the knee joint through its angular movement from extension, mid flexion and through to flexion and then back again.

BACKGROUND ART DISCUSSION

Knee replacement implants are artificial devices that are used to replace a damaged knee or a part of a knee thereof.

A damaged knee joint will contain a combination of bone structure and multiple soft tissue groupings and depending upon where the knee damage arrived from, whether rheumatoid arthritis, osteoarthritis and/or traumatic injury means that every knee replacement or partial knee replacement will either be, if not substantially, at least subtly different albeit ultimately the artificial implants used in the knee replacement will be for the most part of standard sizes.

While an objective of any knee replacement utilising implants would look for an exact reproduction of the structure and operation of a normal healthy knee, as introduced above such a scenario would be very difficult to achieve given the potential differing degrees in the severity of damage to the knee joint and the differences of an individual's bone structures to another.

During surgery, an orthopaedic surgeon when replacing a damaged knee with replacement implants will be required to prepare those bone structures involved in the knee joint to accept the artificial implant including the distal end of the femur, the proximal surface of the tibia and the patella.

This invention focuses on the lower half of the knee hinge joint associated with the proximal surface of the tibia. The correct positioning of the tibial component upon the proximal surface of the tibia assists in providing the best long-term stability of the prosthetic knee joint.

It is recognised that the level of bone resection of the proximal surface of the tibia assists in correct alignment of the tibial component of the prosthetic knee joint to establish an appropriate gap between both the tibial component and the femoral component to ensure stable and secure balanced movement of the knee joint, not only at flexion and extension but at also through out mid-flexion as the knee completes its angular movement between flexion and extension.

Accordingly it is an object of this invention to provide an arrangement and a method such that the proximal surface of the tibia level or profiling of final bone resection of the surface of the tibia provides for optimum tibial component positioning in the total knee arthroplasty such that there is a stable and balanced movement between the tibial component and the femoral component in the prosthetic knee joint throughout the complete arc of motion of the knee from extension, mid-flexion through to flexion.

Further objects and advantages of the invention will become apparent from a complete reading of this specification.

SUMMARY OF THE INVENTION

In one form of the invention there is provided an arrangement for the preparation of the proximal surface of the tibia for a tibial component of a prosthetic knee joint, said arrangement including;

a tibial and femoral stability gap preparation plate, said tibial and femoral stability gap preparation plate adapted to be placed upon an initially resected proximal surface of the tibia, said tibial and femoral stability gap preparation plate further including an upper side, said upper side having a plurality of user operable height adjustable extension tabs, wherein each user operable height adjustable extension tab is adapted to engage an underside of a joint liner, wherein said joint liner includes an upper articulated surface to engage a femoral component of a prosthetic knee joint, such that a height adjustment of said plurality of user operable height adjustable extension tabs defines a stability gap, said defined stability gap provides a stable balanced complete angular movement between a tibial component and a femoral component of the prosthetic knee joint throughout an arc of motion from extension, mid-flexion and flexion;

a stability gap guide drill plate place-able upon the initially resected proximal surface of the tibia subsequent to a withdrawal of the tibial and femoral stability gap preparation plate, said stability gap guide drill plate characterised by including a series of apertures configured to overlap with locations of the corresponding plurality of user operable height adjustable extension tabs when the tibial and femoral stability gap preparation plate was placed upon the initially resected proximal surface of the tibia, said series of apertures adapted to act as a guide for a drill bit to drill a series of bore holes into the proximal surface of the tibia to a depth commensurate with the height adjustment of the user operable height adjustable extension tabs;

a stability gap router plate place-able upon the proximal surface of the tibia subsequent to the withdrawal of the stability gap guide drill plate, said stability gap router plate including a series of vertical mounts adapted to be secured within the series of bore holes drilled into the proximal surface of the tibia to the depth commensurate with the height adjustment of the user operable height adjustable extension tabs such that when the series of vertical mounts are secured within the series of bore holes the stability gap router plate is adapted to allow a router to complete a final bone resection on the surface of the tibia to rout or cut away bone about each of the series of bore holes down to a depth of each of the series of bore holes.

In preference height adjustment of the plurality of user operable height adjustable extension tabs of the tibial and femoral stability gap preparation plate is completed at extension, mid-flexion and flexion.

In preference mid-flexion is normal bending angular movement of an arc between 20° and 80°, preferably 30°.

In preference the tibial and femoral stability gap preparation plate is of a comparable shape and size to the initially resected proximal surface of the tibia.

In preference the arrangement includes four user operable height adjustable extension tabs, wherein each user operable height adjustable extension tab is located generally to a respective corner of the tibial and femoral stability gap preparation plate.

In preference each user operable height adjustable extension tab is telescopically received within a corresponding slot on the upper surface of the tibial and femoral stability gap preparation plate.

In preference each user operable height adjustable extension tab is in communication with a corresponding user engageable knob.

In preference rotational, lateral and/or vertical movement of each user engageable knob translates to a respective extension or retraction of a corresponding user operable height adjustable extension tab.

In preference the rotational, lateral and/or vertical movement of each user engageable knob provides for a mechanical, motorised, hydraulic, pneumatic and/or electronic controlled extension or retraction of the corresponding user operable height adjustable extension tab.

In preference each user operable height adjustable extension tab includes a substantially annular based collar, wherein the substantially annular based collar includes a series of teeth, threads and/or gearing which is adapted to engage a corresponding engagement of teeth, threads and/or gearing of the user engageable knob such that rotation of said user engageable knob translates movement to the substantially annular based collar instigating extension or retraction of the user operable height adjustable extension tab In preference there is a worm gear relationship between the end of the knob and the teeth or geared collar of the respective extension tab.

In preference each user engageable knob includes measurement markings to determine the degree of rotational, lateral and/or vertical movement of each user engageable knob, wherein the measurement markings provide interpretable information with respect to the height adjustment of each user operable height adjustable extension tab based on the degree of rotational, lateral and/or vertical movement of each user engageable knob.

In an alternative embodiment each user engageable knob includes electronic control to determine the degree of rotational, lateral and/or vertical movement of each user engageable knob, wherein the electronic control provides interpretable information with respect to the height adjustment of each user operable height adjustable extension tab based on the degree of rotational, lateral and/or vertical movement of each user engageable knob.

In preference the height indicator includes a series of incremental slots.

In preference these incremental slots provide for a threadable engagement with a peripheral edge of the tibial and femoral stability gap preparation plate.

In preference each user engageable knob includes at its distal end a slot wherein tooling is insertable thereinto to assist in the rotation of the user engageable knob.

The aforelisted preference statements should not be used to limit the scope of the invention which simply requires that the tibial and femoral stability gap plate includes a series of height adjustable extension tabs wherein the ability to adjust the height of these extension tabs is done through a user engageable knob.

In preference the establishing of the appropriate stability gap is determined by making the requisite adjustment, not only at extension and flexion, but also at mid-flexion so that there can be obtained a consistent gap that will provide balance not only at flexion and extension but throughout the arc of angular movement of the knee throughout mid-flexion.

Once the tibial and femoral stability gap preparation plate has determined and been able to define the suitable gap that would be required for the tibial component and the femoral component for balanced and stable movement this measurement of the stability gap is utilised in the final bone resection so that the ultimate outcome is achieved wherein the proximal surface of the tibia will have been resected to provide the requisite profile for the alignment and establishment for correct angular movement of the prosthetic knee joint throughout the entire angular movement and not just at flexion or extension.

Once the defined dimensions of the stability gap have been determined by the user adjusting the height adjustability of each of the extension tabs, this relative height (now depth in the context of the resection into the surface of the tibia) then needs to be resected off the proximal surface of the tibia in order to establish the overall profile of the proximal surface of the tibia for the tibial component to rest thereupon.

As introduced above at first instance there is the stability gap guide drill plate.

In preference the stability gap guide drill plate will also be of comparable dimensions to the tibial and femoral stability gap preparation plate.

In preference the stability gap guide drill plate also includes four apertures generally towards the corner of the stability gap guide drill plate such that when the stability gap guide drill plate is fastened upon the proximal surface of the tibia those holes align themselves in the same position as the corresponding extension tabs were located when the tibial and femoral stability gap preparation plate rested upon the initially resected proximal surface of the tibia.

In preference the stability gap guide drill plate includes fastening screws when secured to the tibia.

As is to be expected once the stability gap guide drill plate is secured upon the proximal surface of the tibia a drill bit can then drill holes to the depth which had been identified by the height adjustment of each of the respective extension tabs that were adjusted by the user when the tibial and femoral stability gap plate was placed upon the initially resected proximal surface of the tibia.

The drill bit would then drill down to a depth commensurate with the adjusted height of each of the respective extension tabs.

Once the stability gap guide drill plate is withdrawn in the preferred embodiment there would then be four drilled bore holes each with a depth that matched the adjusted height of the corresponding extension tab.

In order to complete the final bone resection there would then be the requirement to position into place the stability gap router plate.

Notably the stability gap router plate includes the series of vertical mounts, wherein there is a vertical mount which engages each of the bore holes drilled into the proximal surface of the tibia.

In preference each vertical mount includes at its distal end a plurality of spikes which assist in fastening the stability gap router plate in position upon the proximal surface of the tibia.

In preference the stability router plate includes four vertical mounts each positioned substantially towards a corner of the stability gap router plate such that they align with the drilled bore holes.

As is then to be expected the stability gap router plate includes a series of guides which will then allow a router to complete the bone resection so that all the bone can be cut down to a depth about each of the bore holes so that once the routing is completed the proximal surface of the tibia will have been resected to provide a surface profile that when the tibial component of the prosthetic knee joint is implanted it will be configured so as to present balanced stability between the tibial and femoral components of the prosthetic knee joint.

As the user was able to adjust the height independently for each of the extension tabs not only at flexion and extension but also at mid-flexion instability is avoided throughout the entire arc of motion of the knee joint.

In order now to describe the invention in greater detail a series of preferred embodiments will be shown with the assistance of the following illustrations and accompanying text.

DETAILED DESCRIPTION OF THE DRAWINGS

Figure 1:
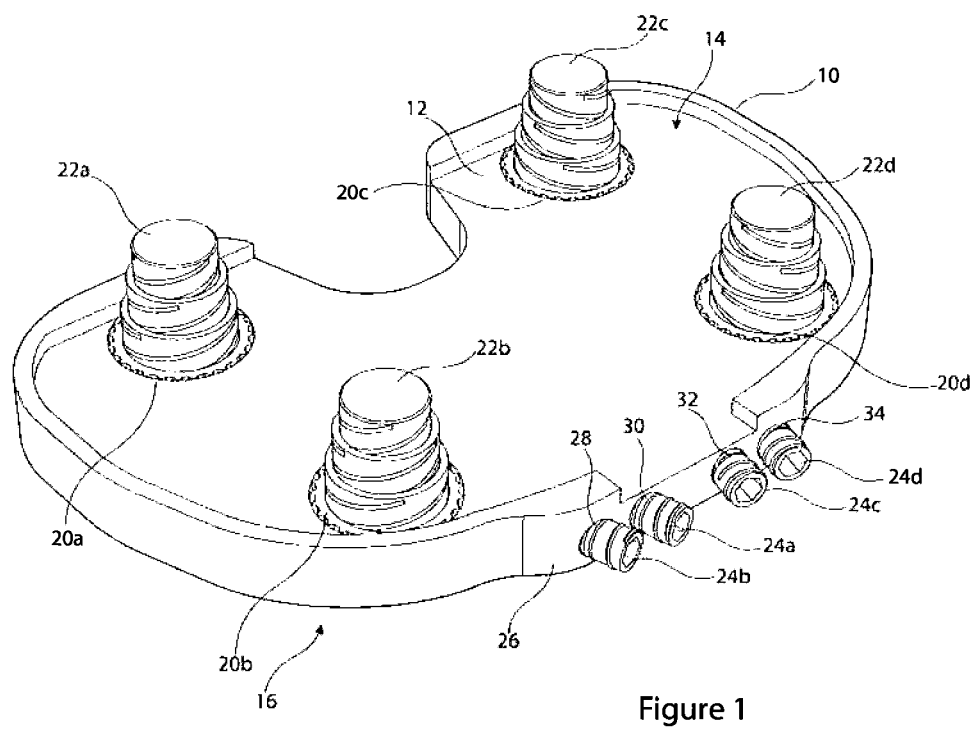
FIG. 1 is a perspective view of the tibial and femoral stability gap preparation plate in a preferred embodiment of the invention.

FIG. 1 shows a perspective view of the tibial and femoral stability gap plate (10).

Orthopaedic surgeons during surgery aim to provide balanced unobstructed movement of the prosthetic knee components throughout the complete arc of motion from extension, mid-flexion and flexion.

The aim is to establish stability that will maintain and ensure balanced stable knee joint movement throughout the arc of motion not only at extension and flexion but also throughout mid-flexion.

Accordingly the bone resection of the proximal surface of the tibia needs to be cut correctly in order to present the appropriate profile to the tibial component positioning in the total knee arthroplasty if the requisite balance is going to be achieved. The tibial and femoral stability gap preparation plate (10) includes the main platform (12) with an upper side (14) and underside (16).

Figure 4:
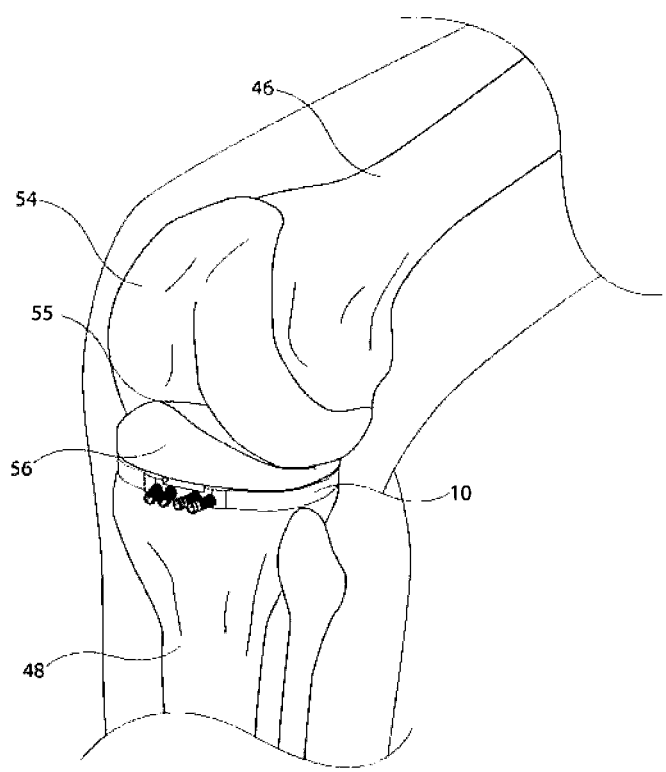
FIG. 4 is a schematic representation showing the tibial and femoral stability gap preparation plate upon the proximal surface of the tibia as well as the joint liner and femoral component of the prosthetic knee joint in a preferred embodiment of the invention.

The underside (16) is configured to rest appropriately as best seen in FIG. 4 upon the proximal surface (50) of the tibia (48).

On the upper surface (14) there is included four slots (20a), (20b), (20c) and (20d) to which telescopically received therein are the corresponding extension tabs (22a), (22b), (22c) and (22d).

Each of the extension tabs are height adjustable through a corresponding user operable knob (24a), (24b), (24c) and (24d).

As will be discussed in greater detail with respect to FIGS. 5a, 5b, 5c and FIG. 6, rotation of knobs (24a), (24b), (24c) and (24d) will adjust the height and the amount of telescopic extension of each of the respective extension tabs (22a), (22b), (22c) and (22d).

Each of the knobs (24a), (24b), (24c) and (24d) are rotatable and supported along the peripheral edge (26) through the respective slot (28), (30), (32) and (34).

Figure 12:
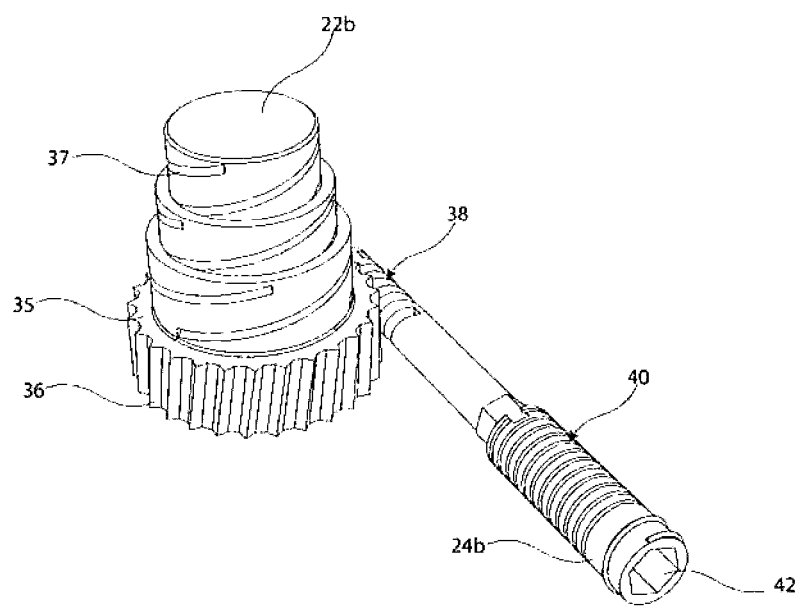
FIG. 12 shows schematic representation of a worm gear arrangement between the extension tabs of the user operable control knobs of the tibial and femoral stability gap preparation plate in a preferred embodiment of the invention

FIG. 12 shows the working relationship of the extension tab (22b) and the corresponding user operable knob (24b) which is representative of the arrangement and operation of the remaining extension tabs (22a), (22c) and (22d).

The user operable knob (24b) includes a series of threads or slotted increments (40) which can be used as a height indicator.

For example, again as will be discussed in greater detail hereafter when the user rotates the operable knob (24b) to adjust the height level of the extension tab (22b) by being able to review the amount of thread or slotted increments left externally from the peripheral rim or collar (26) of the tibial and femoral stability gap preparation plate (10) then the height of the adjustment of the corresponding extension tab (22b) can be determined.

Nonetheless there is a variety of ways in which operable communication between the operating knob and the extension tab as well as means to indicate to indicate the level of height adjustment can be achieved.

For example a cam arrangement, lever arrangement, push and pull systems and the like could all be employed as well as the use of colouring and/or defined unit measurements upon the knob which all can be used to assist in the manipulation of the extension tab through a user operable knob which will be external and accessible from the tibial and femoral stability gap preparation plate (10).

FIG. 12 shows a worm gear arrangement wherein the teeth (36) of the main gear (35) engage with the corresponding thread, teeth or slots (38) of the knob (24b). The gearing arrangement (35) then works with the threaded design (37) of the extension tab (22b) such that ultimately rotation of the user operable knob (24b) will see adjustability of height of the extension tab (22b).

The user operable knob (24b) as with the remaining user operable knobs (24a), (24c) and (24d) each at their distal end include a slot to which tooling can be inserted in, in order to assist in more sensitive stable rotation of the respective user operable knobs (24a), (24b), (24c) and (24d) if required.

While a hand operated control operation is shown it is to be appreciated that adjustment of the user operable knobs could also be motorised and in communication with electronics so that the height adjustment can be recorded digitally. Still further the user operable knobs could be driven pneumatically, hydraulically and the like in other preferred embodiments.

Figure 2:
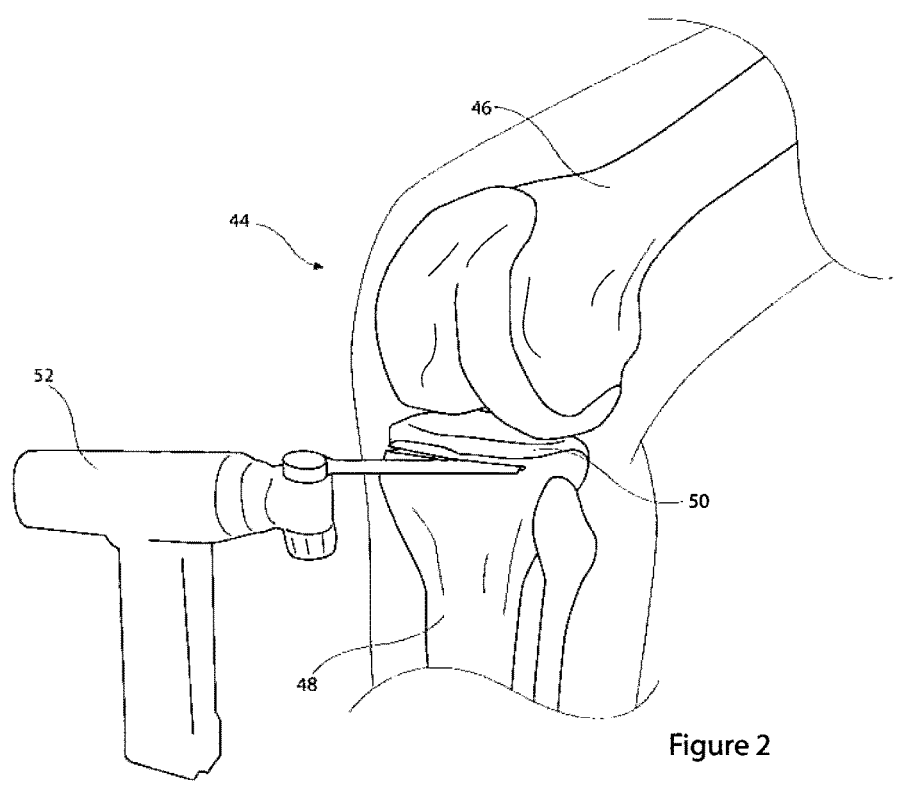
FIG. 2 is a schematic representation of the initial bone resection of the proximal surface of the tibia in a preferred embodiment of the invention.

FIG. 2 shows a knee joint (44) and very generally by way of the cutter (52) anticipates the initial resection of the proximal surface (50) of the tibia (48). The generally distal end of the femur (46) is also shown.

Figure 3:
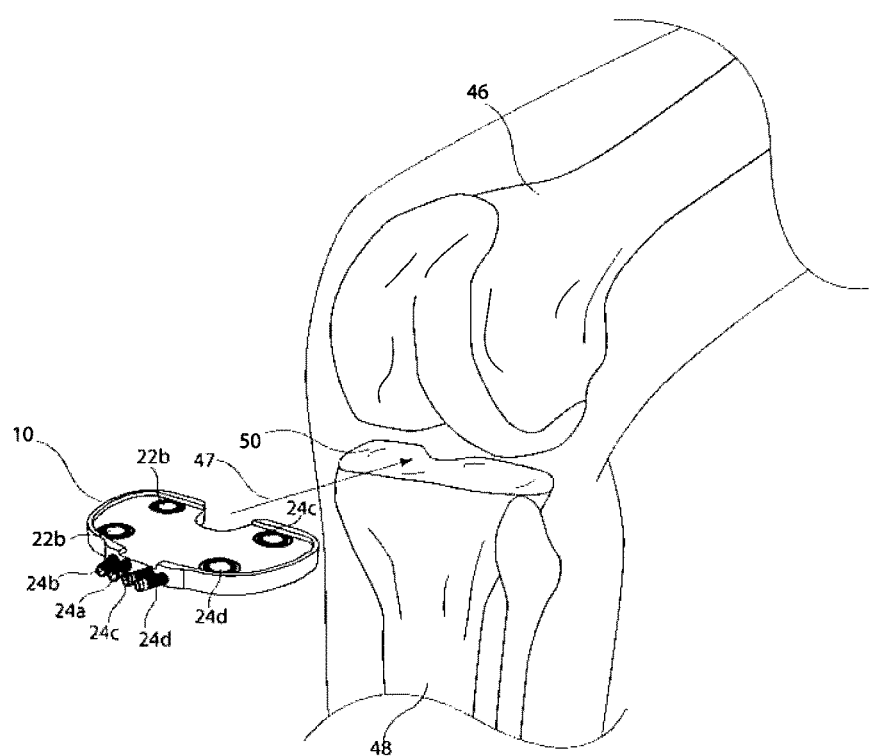
FIG. 3 is a schematic representation showing the inserting of the tibial and femoral stability gap preparation plate subsequent to the initial resection of the proximal surface of the tibia in a preferred embodiment of the invention.

In FIG. 3 the tibial and femoral stability gap preparation plate (10) shown by way of arrow (47) is being inserted onto the proximal surface (50) of the tibia (48).

From FIG. 3 it can be realised that the general shape of the tibial and femoral stability gap preparation plate is of a comparative dimension to the proximal surface (50) of the tibia (48).

FIG. 4 shows the actual positioning of the tibial and femoral stability gap preparation plate (10) on the proximal surface (50) of the tibia (48) and sandwiched therein between the femoral component (54) is the joint liner (56) which has an articulated upper surface (55) to engage the femoral component (54) of the femur (46).

Figures 5A, 5B, 5C:
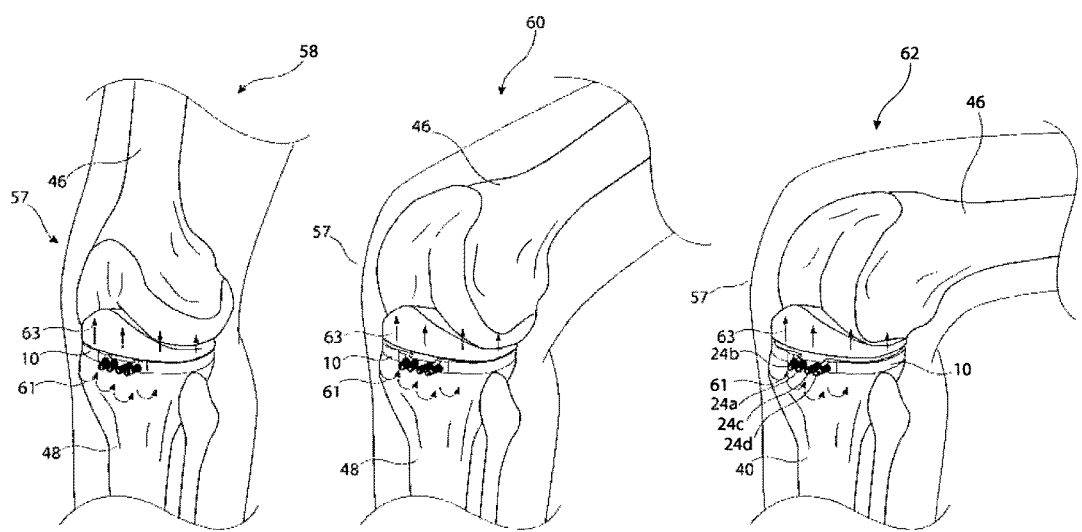
FIGS. 5a, 5b and 5c schematically illustrate user height adjustability of the extension tabs to establish the optimum definable balanced stability gap of the prosthetic knee joint at extension, mid-flexion and flexion respectively in a preferred embodiment of the invention.

FIGS. 5a, 5b, 5c and FIG. 6 illustrate the operable usability of the respective knobs (24a), (24b), (24c) and (24d) when the knee joint (57) is at extension shown by way of (58) for FIG. 5a, mid-flexion shown by way of (60) in FIG. 5b and flexion or 90° shown by way of (62) in FIG. 5c.

Hence the tibial and femoral stability gap preparation plate allows for height adjustability not only at extension (58) and flexion (62) but also along mid-flexion angles or degrees shown only represented generally by (60) in FIG. 5b.

By being able to adjust height at not only flexion and extension but also mid-flexion the final proximal surface of the tibia bone resection will provide for a balanced resection that will ensure that the tibial component insert of the prosthetic knee is stable and balanced throughout the arc of motion in the artificial knee joint operation akin to the appropriate balance that one would expect from a normal healthy knee.

Arrows (61) in FIGS. 5a, 5b and 5c show how the user operable knobs (24a), (24b), (24c) and (24d) can easily be rotated which this then correlates to height adjustable movement of each of the respective extension tabs (22a), (22b), (22c) and (22d) shown by way of arrows (63).

Figure 6:
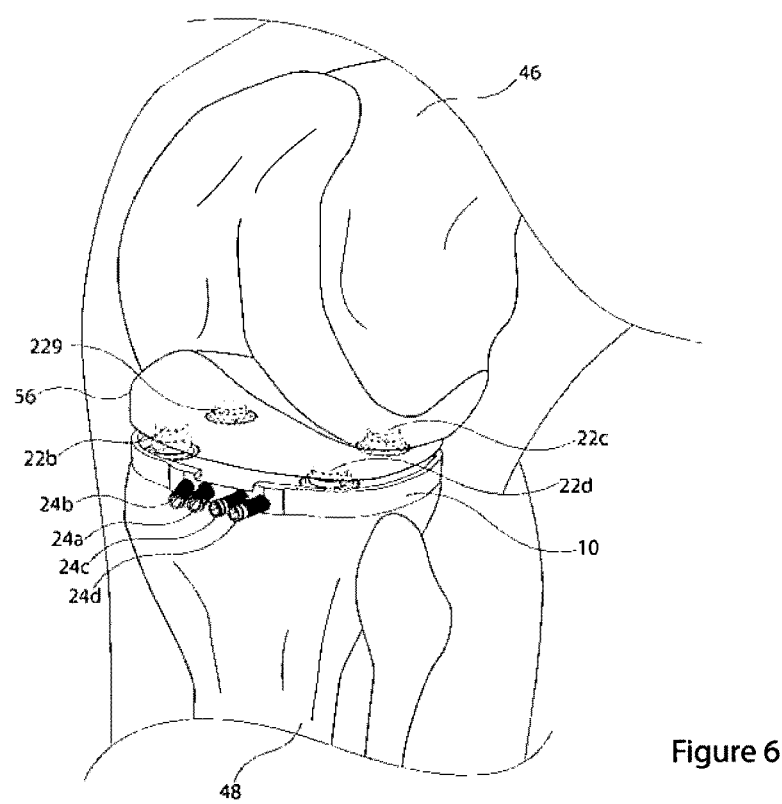
FIG. 6 shows a part see-through view of the adjustability of the extension tabs of the tibial and femoral stability gap preparation plate in a preferred embodiment of the invention.

FIG. 6 also helps appreciate through the part see-through view wherein the extension tabs (22a), (22b), (22c) and (22d) can be extended independently relative to the other in order to define the appropriate gap that will bring the requisite final bone resection to obtain the necessary balance to ensure stable knee movement throughout the arc of motion of the artificial joint.

Figure 7:
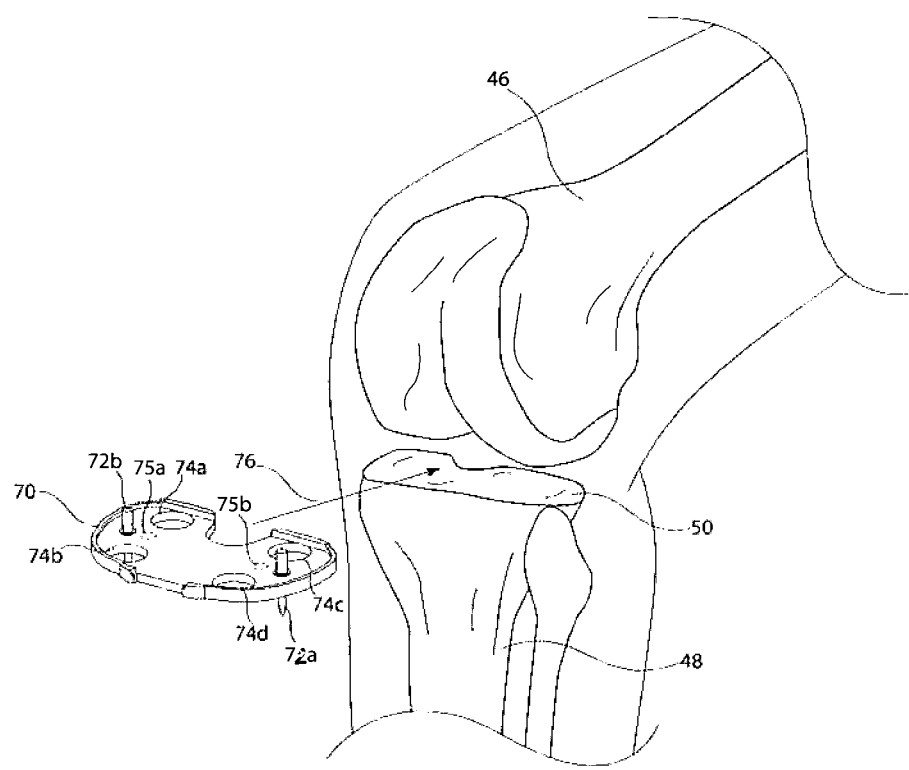
FIG. 7 shows a schematic representation of the stability gap guide drill plate being positioned on the initially resected proximal surface of the tibia subsequent to the withdrawal of the tibial and femoral stability gap preparation plate in a preferred embodiment of the invention.

Once the extension tabs (22a), (22b), (22c) and (22d) have established their requisite heights the tibial and femoral stability gap preparation plate (10) can be withdrawn and which as seen in FIG. 7 the stability gap guide drill plate (70) shown by way of arrow (76) can be introduced onto the proximal surface (50) of the tibia (48).

Figure 8:
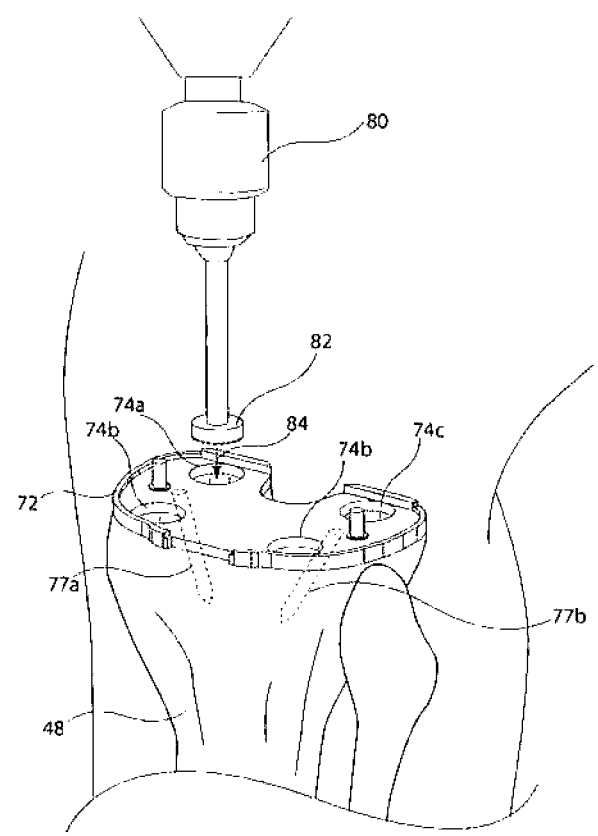
FIG. 8 illustrates a schematic representation of the drilling of the bore holes on the proximal surface of the tibia to a depth commensurate with the established height of a corresponding extension tab of the tibial and femoral stability gap preparation plate in a preferred embodiment of the invention.

The stability gap guide drill plate (70) is generally secured through positioning pins (72a) and (72b) but as seen in FIG. 8 more substantial screws shown by way of the broken lines (77a) and (77b) can be inserted in order to make sure that the stability gap guide drill plate (70) is appropriately secured in place prior to any drilling.

FIG. 8 helps in understanding as to how the stability gap guide drill plate (72) has the same apertures (74a), (74b), (74c) and (74d) which match up with the slot positions (20a), (20b), (20c) and (20d) to which the extension tabs extended therefrom.

The drill (80) and the drill bit (82) is then able to drill into the proximal surface (50) of the tibia (48) to a depth commensurate with the height extension that was defined on the corresponding extension tab (24a), (24b), (24c) and (24d).

Figure 9:
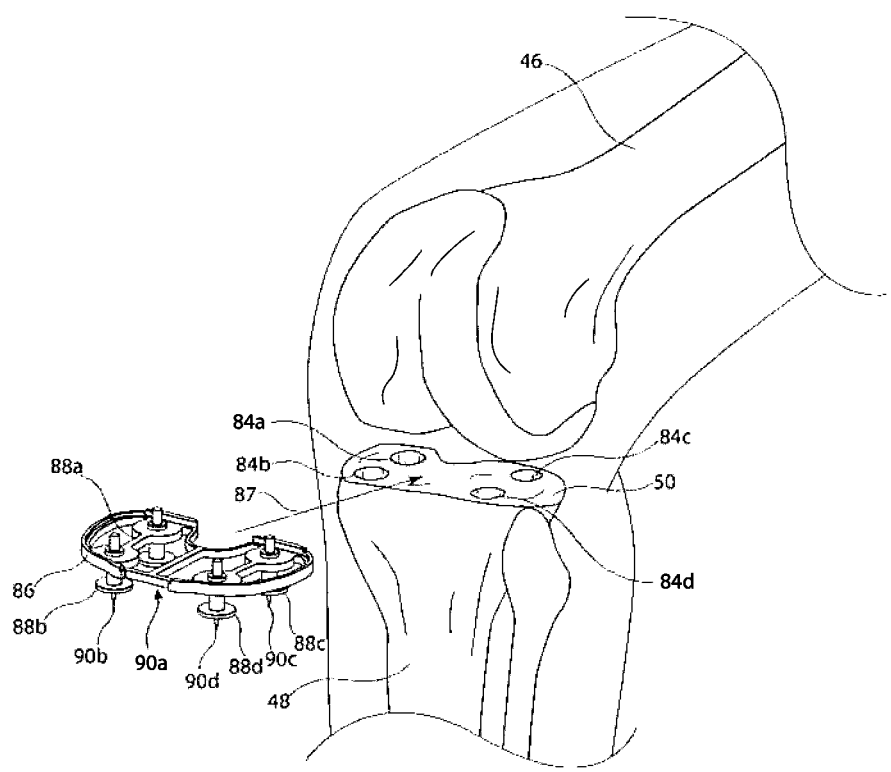
FIG. 9 shows the schematic representation of the positioning of the stability gap router plate subsequent to the establishment of the bored holes drilled within the proximal surface of the tibia in a preferred embodiment of the invention.

As seen in FIG. 9 once the holes (84a), (84b), (84c) and (84d) have been drilled into the proximal surface (50) of the tibia (48) the stability gap router plate (88) shown by way of arrow (87) can be inserted to be positioned in place upon the proximal surface (50) of the tibia (48).

Vertical mounts (88a), (88b), (88c) and (88d) slot into each of the respective bore holes (84a), (84b), (84c) and (84d) to the set depth level.

Setting pines (90a), (90b), (90c) and (90d) for each of the respective vertical mounts (88a), (88b), (88c) and (88d) position the vertical mounts in place within the respective bored holes (84a), (84b), (84c) and (84d).

Figure 10:
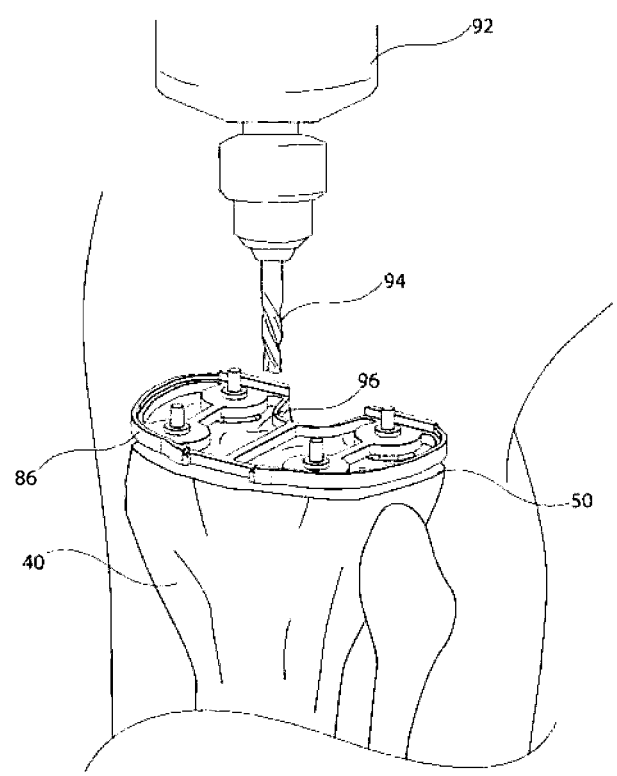
FIG. 10 shows a schematic representation of a router working in conjunction with the stability gap router plate in a preferred embodiment of the invention.
Figure 11:
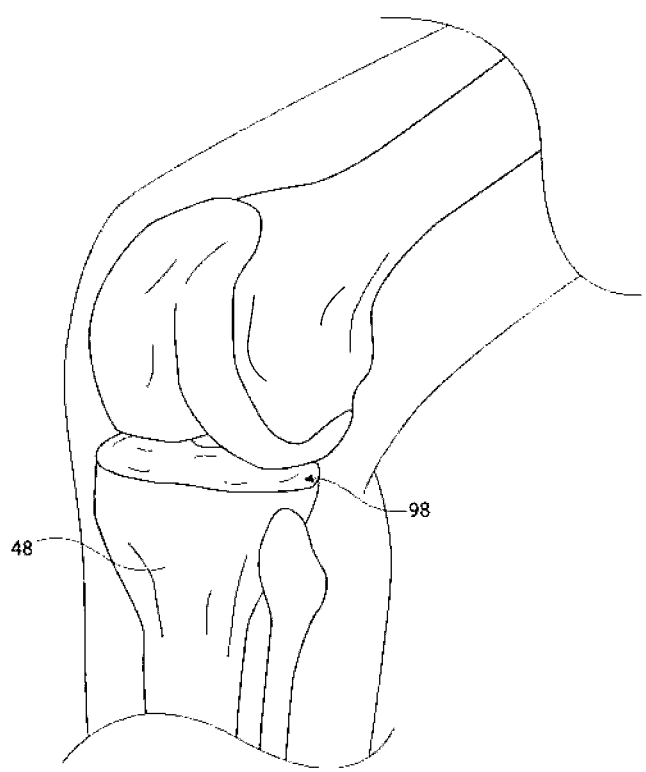
FIG. 11 shows a schematic representation of the final bone resection of the proximal surface of the tibia in a preferred embodiment of the invention.

As best seen in FIG. 10 the router (92) through its routing piece (94) can then move about the stability gap router guide plate (86) to carve out all the remaining bone (96) on the proximal surface (50) of the tibia (58) so as to establish the final bone resection profile represented as (98) upon the tibia (48) as seen in FIG. 11.

The words rout, router, drill and drilling are used unrestrictedly and should not be interpreted narrowly. Any tooling, plate and mounting arrangement that can provide the requisite support structure, bore holes and/or cut away bone to achieve the outcome of this invention in providing the final bone resection profile are intended to fall within the spirit and scope of this invention as described and defined by this terminology.

This established bone resection will provide a levelling or proximal surface profile which will allow the tibial component positioning within the total knee arthroplasty which as introduced above will ensure that the tibial component insert upon the proximal surface of the tibia will be stable throughout the arc of motion of the knee joint and also present the requisite balancing and stability to allow stable angular movement of the knee joint not only at extension and flexion but also throughout the mid-flexion range of movement.

The invention claimed is:

1. An arrangement for the preparation of the proximal surface of a tibia for a tibial component of a prosthetic knee joint, said arrangement including;
   a tibial and femoral stability gap preparation plate, said tibial and femoral stability gap preparation plate adapted to be placed upon an initially resected proximal surface of the tibia, said tibial and femoral stability gap preparation plate further including an upper side, said upper side having a plurality of user operable height adjustable extension tabs, wherein each user operable height adjustable extension tab is adapted to engage an underside of a joint liner, wherein said joint liner includes an upper articulated surface to engage a femoral component of a prosthetic knee joint, such that a height adjustment of said plurality of user operable height adjustable extension tabs defines a stability gap, said defined stability gap provides a stable balanced complete angular movement between a tibial component and a femoral component of the prosthetic knee joint throughout an arc of motion from extension, mid-flexion and flexion;

a stability gap guide drill plate place-able upon the initially resected proximal surface of the tibia subsequent to a withdrawal of the tibial and femoral stability gap preparation plate, said stability gap guide drill plate characterised by including a series of apertures configured to overlap with locations of the corresponding plurality of user operable height adjustable extension tabs when the tibial and femoral stability gap preparation plate was placed upon the initially resected proximal surface of the tibia, said series of apertures adapted to act as a guide for a drill bit to drill a series of bore holes into the proximal surface of the tibia to a depth commensurate with the height adjustment of the user operable height adjustable extension tabs;

a stability gap router plate place-able upon the proximal surface of the tibia subsequent to the withdrawal of the stability gap guide drill plate, said stability gap router plate including a series of vertical mounts adapted to be secured within the series of bore holes drilled into the proximal surface of the tibia to the depth commensurate with the height adjustment of the user operable height adjustable extension tabs such that when the series of vertical mounts are secured within the series of bore holes the stability gap router plate is adapted to allow a router to complete a final bone resection on the surface of the tibia to rout or cut away bone about each of the series of bore holes down to a depth of each of the series of bore holes.

2. The arrangement of claim 1 wherein the tibial and femoral stability gap preparation plate is of a comparable shape and size to the initially resected proximal surface of the tibia.

3. The arrangement of claim 1 wherein the arrangement includes four user operable height adjustable extension tabs, wherein each user operable height adjustable extension tab is located generally to a respective corner of the tibial and femoral stability gap preparation plate.

4. The arrangement of claim 1 wherein each user operable height adjustable extension tab is telescopically received within a corresponding slot on the upper surface of the tibial and femoral stability gap preparation plate.

5. The arrangement of claim 1 to wherein each user operable height adjustable extension tab is in communication with a corresponding user engageable knob.

6. The arrangement of claim 5 wherein rotational, lateral and/or vertical movement of each user engageable knob translates to a respective extension or retraction of a corresponding user operable height adjustable extension tab.

7. The arrangement of claim 6 wherein the rotational, lateral and/or vertical movement of each user engageable knob provides for a mechanical, motorised, hydraulic, pneumatic and/or electronic controlled extension or retraction of the corresponding user operable height adjustable extension tab.

8. The arrangement of claim 7 wherein each user operable height adjustable extension tab includes a substantially annular based collar, wherein the substantially annular based collar includes a series of teeth, threads and/or gearing which is adapted to engage a corresponding engagement of teeth, threads and/or gearing of the user engageable knob such that rotation of said user engageable knob translates movement to the substantially annular based collar instigating extension or retraction of the user operable height adjustable extension tab.

9. The arrangement of claim 6 wherein each user engageable knob includes measurement markings to determine the degree of rotational, lateral and/or vertical movement of each user engageable knob, wherein the measurement markings provide interpretable information with respect to the height adjustment of each user operable height adjustable extension tab based on the degree of rotational, lateral and/or vertical movement of each user engageable knob.

10. The arrangement of claim 6 wherein each user engageable knob includes electronic control to determine the degree of rotational, lateral and/or vertical movement of each user engageable knob, wherein the electronic control provides interpretable information with respect to the height adjustment of each user operable height adjustable extension tab based on the degree of rotational, lateral and/or vertical movement of each user engageable knob.

11. The arrangement of claim 9 wherein each user engageable knob includes at its distal end a slot wherein tooling is insertable thereinto to assist in the rotation of the user engageable knob.

12. The arrangement of claim 9 wherein the stability gap guide drill plate is of comparable dimensions to the tibial and femoral stability gap preparation plate.

13. The arrangement of claim 12 wherein the stability gap guide drill plate includes four apertures generally towards the corner of the stability gap guide drill plate such that when the stability gap guide drill plate is fastened upon the proximal surface of the tibia said four apertures align in locations to the corresponding user operable height adjustable extension tab when the tibial and femoral stability gap preparation plate rested upon the initially resected proximal surface of the tibia.

14. The arrangement of claim 12 further comprising fastening screws securing the stability gap guide drill plate to the tibia.

15. The arrangement of claim 1 wherein each of the series of vertical mounts of the stability gap router plate includes at its distal end a spike to assist in fastening the stability gap router plate in position upon the proximal surface of the tibia.

16. The arrangement of claim 1 wherein height adjustment of the plurality of user operable height adjustable extension tabs of the tibial and femoral stability gap preparation plate is completed at extension, mid-flexion and flexion.

17. The arrangement of claim 16 wherein mid-flexion is normal bending angular movement of an arc between 20° and 80°.

* * * * *